(12) United States Patent
Donaldson

(10) Patent No.: US 12,012,270 B2
(45) Date of Patent: Jun. 18, 2024

(54) MEDICAL ELECTRODE TEAR STRIP

(71) Applicant: CONMED CORPORATION, Utica, NY (US)

(72) Inventor: Timothy A. Donaldson, Clinton, OH (US)

(73) Assignee: CONMED CORPORATION, Utica, NY (US)

( * ) Notice: Subject to any disclaimer, the term of this patent is extended or adjusted under 35 U.S.C. 154(b) by 0 days.

(21) Appl. No.: 16/752,735

(22) Filed: Jan. 27, 2020

(65) Prior Publication Data

US 2020/0324952 A1 Oct. 15, 2020

Related U.S. Application Data

(60) Provisional application No. 62/782,489, filed on Dec. 20, 2018.

(51) Int. Cl.
| | | |
|---|---|---|
| *B65D 73/02* | (2006.01) | |
| *A61B 5/282* | (2021.01) | |
| *A61N 1/04* | (2006.01) | |
| *B65D 75/42* | (2006.01) | |
| *B65D 75/58* | (2006.01) | |
| *B65D 75/66* | (2006.01) | |
| *B65D 75/04* | (2006.01) | |
| *B65D 81/32* | (2006.01) | |

(52) U.S. Cl.
CPC .......... *B65D 75/5811* (2013.01); *A61B 5/282* (2021.01); *A61B 2562/242* (2013.01); *A61N 1/046* (2013.01); *B65D 75/04* (2013.01); *B65D 75/66* (2013.01); *B65D 81/3261* (2013.01)

(58) Field of Classification Search
CPC .. B65D 33/002; B65D 75/5811; B65D 75/42;
B65D 75/527; B65D 75/66; B65D 75/5805; B65D 75/68; B65D 75/30; B65D 81/3261; A61B 5/04085; A61B 2562/242; A61B 5/282; A61B 5/285; A47J 36/30; A47J 36/06; A47J 36/02; A47J 36/022; A47J 36/2477; A47J 36/34; A47J 36/2405; A61N 1/0472; A61N 1/046; A61N 1/0492
USPC ......... 383/38, 41, 204–206, 209; 220/359.4; 206/820, 701, 438, 363, 210, 727, 484; 600/391, 393, 397; 607/142, 148, 152
See application file for complete search history.

(56) References Cited

U.S. PATENT DOCUMENTS

| | | | | |
|---|---|---|---|---|
| 2,293,952 | A | * | 8/1942 | Stroop .................. B65D 75/66 383/210 |
| 2,791,324 | A | * | 5/1957 | Dow .................... B65D 75/323 206/568 |
| 3,162,306 | A | * | 12/1964 | Zackheim ............. A61F 15/001 206/440 |

(Continued)

*Primary Examiner* — Gideon R Weinerth
(74) *Attorney, Agent, or Firm* — Bond, Schoeneck & King, PLLC; Frederick J. M. Price

(57) ABSTRACT

A dispenser device for opening multiple packs of medical electrodes in a single action. The dispenser device includes a plurality of connected pouches including a first terminal pouch and a second terminal pouch. An electrode is disposed within each pouch and a seal extends along each pouch. The dispenser device also includes a tear strip that is substantially aligned with at least a portion of the seal. The tear strip can extend across all pouches. In one single tearing or pulling motion along the tear strip, each pouch of the plurality of connected pouches can be opened.

6 Claims, 1 Drawing Sheet

(56) References Cited

U.S. PATENT DOCUMENTS

| | | | | |
|---|---|---|---|---|
| 3,162,539 A * | 12/1964 | Repko | B65D 75/42 | 426/119 |
| 3,291,377 A * | 12/1966 | Eggen | B65D 75/68 | 426/123 |
| 3,396,836 A * | 8/1968 | Cook | B65D 81/3261 | 206/820 |
| 3,416,651 A * | 12/1968 | Valdemar | B65D 75/68 | 206/820 |
| 3,426,959 A * | 2/1969 | Lemelson | B65D 75/66 | 383/905 |
| 3,494,538 A * | 2/1970 | Matthews | B65D 75/66 | 206/481 |
| 3,533,877 A * | 10/1970 | Cook | B32B 27/00 | 156/313 |
| 3,565,329 A * | 2/1971 | Wagner, Jr. | B65D 75/68 | 57/212 |
| 3,674,135 A * | 7/1972 | Simon | B65D 83/0882 | 206/225 |
| 3,685,645 A * | 8/1972 | Kawaguchi | B65D 75/5805 | 206/210 |
| 3,779,449 A * | 12/1973 | Membrino | B65D 33/002 | 383/35 |
| 4,339,035 A * | 7/1982 | Marcus | B65D 83/0847 | 206/390 |
| 4,409,981 A * | 10/1983 | Lundberg | A61B 5/273 | 600/397 |
| 4,441,500 A * | 4/1984 | Sessions | A61B 5/25 | 600/394 |
| 4,543,958 A * | 10/1985 | Cartmell | A61B 5/259 | 600/397 |
| 4,721,111 A * | 1/1988 | Muttitt | A61B 5/265 | 600/397 |
| 4,727,881 A * | 3/1988 | Craighead | A61B 5/04087 | 600/392 |
| 4,731,926 A * | 3/1988 | Sibalis | A61N 1/325 | 600/397 |
| 4,779,630 A * | 10/1988 | Scharnberg | A61N 1/046 | 607/142 |
| 4,798,208 A * | 1/1989 | Faasse, Jr. | A61B 5/0408 | 600/392 |
| 4,798,642 A * | 1/1989 | Craighead | A61B 5/259 | 156/289 |
| 4,848,353 A * | 7/1989 | Engel | C09J 4/00 | 600/397 |
| 4,903,841 A * | 2/1990 | Ohsima | B65D 75/5805 | 229/237 |
| 4,911,178 A * | 3/1990 | Neal | A61N 1/05 | 150/131 |
| 4,972,657 A * | 11/1990 | McKee | B65D 33/002 | 53/449 |
| 5,116,140 A * | 5/1992 | Hirashima | B65D 75/66 | 383/66 |
| 5,135,790 A * | 8/1992 | Kaplan | B65D 75/66 | 229/238 |
| 5,178,144 A * | 1/1993 | Cartmell | A61B 5/25 | 600/392 |
| 5,191,887 A * | 3/1993 | Cartmell | A61B 5/0408 | 600/392 |
| 5,226,225 A * | 7/1993 | Bryan | A61B 5/259 | 29/878 |
| 5,255,677 A * | 10/1993 | Schaefer | A61B 5/296 | 607/152 |
| 5,462,157 A * | 10/1995 | Freeman | B65D 75/20 | 600/391 |
| 5,827,184 A * | 10/1998 | Netherly | A61B 5/25 | 607/152 |
| 5,928,142 A * | 7/1999 | Cartmell | A61B 5/274 | 607/152 |
| 5,984,102 A * | 11/1999 | Tay | A61N 1/0472 | 206/439 |
| 6,228,458 B1 * | 5/2001 | Pinchen | B29C 59/007 | 206/245 |
| 6,415,170 B1 * | 7/2002 | Loutis | A61B 5/259 | 600/397 |
| 6,675,051 B2 * | 1/2004 | Janae | A61N 1/0492 | 607/152 |
| 6,874,621 B2 * | 4/2005 | Solosko | A61B 5/266 | 206/701 |
| 6,935,889 B2 * | 8/2005 | Picardo | A61N 1/046 | 600/392 |
| 6,965,799 B2 * | 11/2005 | Nova | A61B 5/257 | 607/148 |
| 6,993,395 B2 * | 1/2006 | Craige, III | A61N 1/0492 | 607/152 |
| 7,032,810 B2 * | 4/2006 | Benedetti | B65D 77/32 | 229/242 |
| D522,374 S * | 6/2006 | Nova | A61N 1/046 | D9/629 |
| 8,238,998 B2 * | 8/2012 | Park | A61B 5/291 | 607/152 |
| 8,260,438 B2 * | 9/2012 | Meyer | A61N 1/0472 | 607/142 |
| 8,320,988 B2 * | 11/2012 | Axelgaard | A61N 1/0452 | 607/152 |
| 8,371,448 B1 * | 2/2013 | Reaux | A61B 50/15 | 206/370 |
| 8,428,751 B2 * | 4/2013 | Copp-Howland | A61N 1/046 | 607/142 |
| 8,594,812 B2 * | 11/2013 | Meyer | A61N 1/0472 | 607/152 |
| D780,596 S * | 3/2017 | Sam | D9/709 | |
| 10,071,833 B2 * | 9/2018 | Haedt | B65D 75/5805 | |
| D829,917 S * | 10/2018 | Duck | D24/187 | |
| D837,660 S * | 1/2019 | Abed | D9/709 | |
| D863,979 S * | 10/2019 | Reaux | D9/709 | |
| D883,655 S * | 5/2020 | Lotosky-Compton | D3/203.1 | |
| 2002/0117408 A1 * | 8/2002 | Solosko | A61B 5/0408 | 206/210 |
| 2004/0260376 A1 * | 12/2004 | Craige, III | A61N 1/046 | 600/382 |
| 2005/0220377 A1 * | 10/2005 | Hanus | B65D 75/66 | 383/206 |
| 2005/0283219 A1 * | 12/2005 | O'Connor | A61B 5/291 | 607/148 |
| 2006/0098902 A1 * | 5/2006 | Leighton | B65D 75/66 | 383/204 |
| 2006/0142831 A1 * | 6/2006 | Nova | A61B 5/0408 | 607/142 |
| 2006/0222272 A1 * | 10/2006 | Kim | B65D 75/66 | 383/205 |
| 2006/0239594 A1 * | 10/2006 | Ishizaki | B65D 33/2533 | 383/203 |
| 2008/0210592 A1 * | 9/2008 | Anderson | A61N 1/046 | 206/701 |
| 2009/0074333 A1 * | 3/2009 | Griebel | B65D 75/008 | 383/200 |
| 2010/0094388 A1 * | 4/2010 | Hauge | A61N 1/0492 | 493/379 |
| 2012/0217180 A1 * | 8/2012 | Kurose | B65B 61/02 | 428/43 |
| 2012/0267272 A1 * | 10/2012 | Agrawal | A61B 50/30 | 206/439 |
| 2013/0043155 A1 * | 2/2013 | Hartley | A61B 50/39 | 206/363 |
| 2013/0283736 A1 * | 10/2013 | VanLoocke | B65B 29/10 | 383/204 |
| 2013/0341237 A1 * | 12/2013 | Krumme | A61J 1/035 | 206/530 |
| 2014/0174042 A1 * | 6/2014 | Ezaki | B65D 33/16 | 383/207 |
| 2014/0312050 A1 * | 10/2014 | Coggins | A61B 50/30 | 221/71 |
| 2020/0002073 A1 * | 1/2020 | Wood | B65B 11/50 | |
| 2020/0163438 A1 * | 5/2020 | Peralta | A45D 40/24 | |
| 2020/0324952 A1 * | 10/2020 | Donaldson | A61B 5/0408 | |
| 2021/0354905 A1 * | 11/2021 | Hart | B65D 83/0472 | |

* cited by examiner

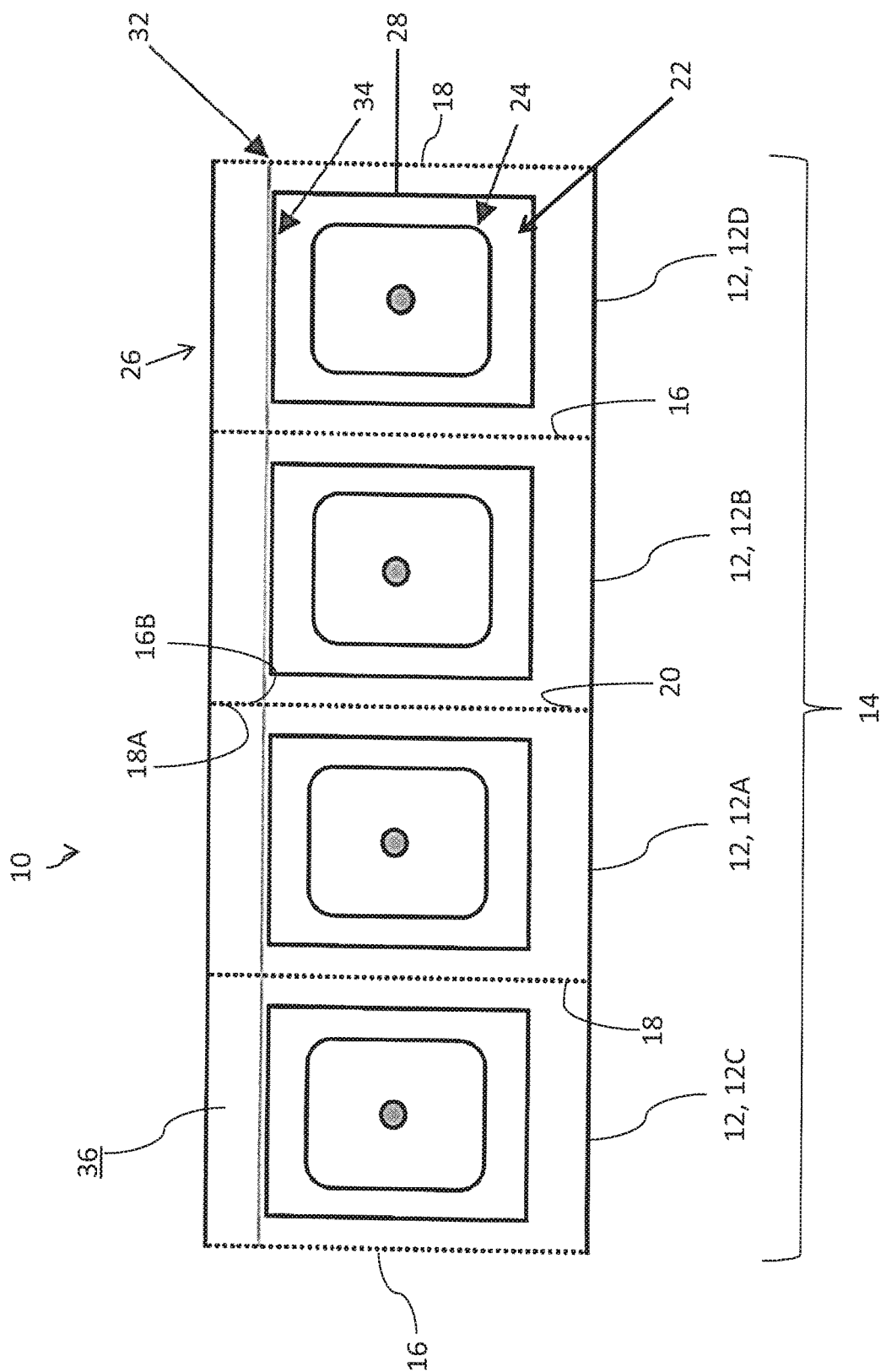

MEDICAL ELECTRODE TEAR STRIP

CROSS-REFERENCE TO RELATED APPLICATION

The present application claims priority to and the benefit of U.S. Provisional Patent Application No. 62/782,489, filed on Dec. 20, 2018 and entitled "Medical Electrode Tear Strip," the entirety of which is incorporated herein by reference.

BACKGROUND OF THE INVENTION

1. Field of the Invention

The present invention relates to medical electrodes and, more particularly, to a dispenser device for opening multiple packs of medical electrodes in a single action.

2. Description of Related Art

Medical electrodes are typically used in electrocardiography and like diagnostic procedures as well as for long-term monitoring where a patient must be electrically connected to a test or monitoring device. For a given procedure, a patient may require anywhere from two (2) to eleven (11) medical electrodes. The clinical use of medical electrodes requires many different packaging configurations. Medical electrodes are typically packaged in quantities of three (3), five (5), ten (10), and fifty (50). Depending on clinician preference, a physician or hospital may choose to have one or multiple of these configurations available. Often, clinicians will need to open multiple packages of electrodes to get the desired number for a procedure. Having to open multiple packages is time consuming and introduces a much greater risk of dropping an electrode, rendering it unusable.

Therefore, there is a need for a dispenser device for dispensing only the amount of medical electrodes necessary for a given procedure.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

The present disclosure is directed to an inventive configuration, structure, and resulting function of a dispenser device for opening multiple packs of medical electrodes in a single action. According to one aspect, the dispenser device includes a plurality of connected pouches including a first terminal pouch and a second terminal pouch. An electrode is within each pouch and a seal extends along each pouch. The dispenser device also includes a tear strip that is substantially aligned with at least a portion of the seal. The tear strip extends across all pouches. In one single tearing or pulling motion along the tear strip, each pouch of the plurality of connected pouches can be opened.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which:

FIG. 1 is a top view schematic representation of a dispenser device, according to an embodiment.

DETAILED DESCRIPTION OF THE INVENTION

Referring now to the drawings, wherein like reference numerals refer to like parts throughout, there is seen in FIG. 1 a top view schematic representation of a dispenser device 10, according to an embodiment. The dispenser device 10 includes one or more connected pouches 12. The pouches 12 may be composed of paper, polypropylene, or foil. The dispenser device 10 shown in FIG. 1 comprises four connected pouches 12. However, the dispenser device 10 can include any number of pouches 12. For example, the dispenser device 10 can include quantities of three (3), five (5), ten (10), and fifty (50) connected pouches 12.

In the depicted embodiment, each pouch 12 of the dispenser device 10 is rectangular. In the embodiment wherein the dispenser device 10 comprises a plurality of rectangular pouches 12, the pouches 12 are connected in a strip 14, as shown in FIG. 1. Specifically, each pouch 12 has a first side 16 and an opposing second side 18. To create the strip 14, the second side 18A of a first pouch 12A is connected to the first side 16B of a second pouch 12B. In some embodiments, there are perforations 20 extending between the second side 18A of the first pouch 12A and the first side 16B of the second pouch 12B such that a user may adjust the number of pouches 12 in the strip 14 to the required and/or desired amount for a particular procedure. Although rectangular pouches 12 are shown arranged in the strip 14 in FIG. 1, the pouches 12 can have any type of geometry suitable to house a medical electrode 24 therein and still be connected in the strip 14.

Still referring to FIG. 1, each pouch 12 comprises an inner volume 22. The inner volume 22 of each pouch 12 is sized and configured to fit the medical electrode 24 therein. In the rectangular embodiment of the pouches 12 shown in FIG. 1, the inner volume 22 of each pouch 12 receives a medical electrode 24 prior to sealing of the pouch 12. In an embodiment, the pouch 12 receives a medical electrode 24 from a sealable top end 26 of the pouch 12. In an alternative embodiment, the pouch 12 is composed of two layers, a top and bottom layer (not shown), and the medical electrode 24 is placed between the two layers prior to sealing. After each pouch 12 receives the medical electrode 24, the pouch 12 is sealed. In a preferred embodiment, the pouches 12 are thermally sealed. In some embodiments, a thermal seal 28 extending across the top end 26 of the pouch 12 and in other embodiments, the thermal seal 28 can extend around the entire perimeter 30 of the medical electrode 24.

As shown in FIG. 1, the dispenser device 10 includes a single-action opening mechanism. In the depicted embodiment, the opening mechanism is a tear strip 32. In some embodiments, the tear strip 32 is a scored band. In other embodiments, the tear strip 32 is an added length of material, such as a narrow ribbon. In some instances, the tear strip 32 is composed of polymers, such as polypropylene, but other filaments can be used. The tear strip 32 may also be composed of adhesive tape using a heat activated adhesive system (e.g., pressure sensitive adhesive).

As shown in FIG. 1, the tear strip 32 extends across the pouch 12 from the first side 16 to the opposing second side 18. The tear strip 32 is substantially aligned with at least a portion 34 of the thermal seal 28. In the depicted embodiment, the tear strip 32 is substantially aligned with the portion 34 of the thermal seal 28 extending between the medical electrode 24 and the top end 26 of the pouch 12. It is preferable that the tear strip 32 be positioned such that tearing the tear strip 32 breaks the portion 34 of the thermal seal 28.

In the embodiment shown in FIG. 1, the tear strip 32 extends entirely across the dispenser device 10 from the first side 16 of a first terminal pouch 12C to the second side 18 of a second terminal pouch 12D. With the tear strip 32 extending across multiple pouches 12, one single linear action of tearing or pulling of the tear strip 32 from the first side 16 of the first terminal pouch 12C to the second side 18 of the second terminal pouch 12D will break open the portion 34 of the terminal seal 28 on all pouches 12 of the dispenser device 10. As shown in FIG. 1, the tear strip 32 extends from the first side 16 to the second side 18 of the dispenser device 10 (or stated differently, from the first side 16 of the first terminal pouch 12C to the second side 18 of the second terminal pouch 12D) such that the tearing or pulling action may be initiated at the first side 16 of the dispenser device 10 (or first terminal pouch 12C) or the second side 18 of the dispenser device 10 (or the second terminal pouch 12D). A single tear strip 32 extending across all pouches 12 aligned with the portion 34 of the thermal seal 28 provides the cleanest edge for the pouch 12 when the pouch 12 is opened.

In FIG. 1, the tear strip 32 extends across an exterior surface 36 of the pouches 12. In alternative embodiments, the tear strip 32 can extend along an interior surface (not shown) of the pouches 12. In the embodiments wherein the tear strip 32 is on the interior surface of the pouches 12, the tear strip 32 is still substantially aligned with the portion 34 of the thermal seal 28. The tear strip 32 is held in place by cross-seals on the pouch 12.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A dispenser device comprising a plurality of pouches, each pouch having a first side and a second side wherein each of the plurality of pouches is connected along one of its first side or its second side to the first side or the second side of another of the plurality of pouches to form a continuous strip having a first terminal pouch and a second terminal pouch;
    a plurality of electrodes, wherein each electrode is disposed within a corresponding one of the plurality of pouches;
    a seal extending on a longitudinal axis across a top edge of each pouch of the plurality of connected pouches; and
    a single tear strip comprising a separate length of material extending across a surface of all of the plurality of connected pouches from the first side of the first terminal pouch to the second side of the second terminal pouch and said tear strip having a first edge being aligned with the seal so that removal of the tear strip will break the seal and permit access to all of the pouches in the continuous strip.

2. The device of claim 1, wherein the seal is a thermal seal.

3. The device of claim 1, wherein at least one pouch of the plurality of connected pouches is rectangular shaped.

4. The device of claim 1, wherein the seal extends along an exterior surface of each pouch of the plurality of connected pouches.

5. The device of claim 1, wherein the tear strip extends across an exterior surface of at least one of the plurality of connected pouches.

6. The device of claim 1, wherein the tear strip extends across an interior surface of at least one of the plurality of connected pouches.

* * * * *